(12) United States Patent
Vesala (10) Patent No.: US 8,302,495 B2
(45) Date of Patent: Nov. 6, 2012

(54) DILUTING SAMPLER AND A METHOD FOR COLLECTING AND DILUTING A GASEOUS SAMPLE

(75) Inventor: Hannu Vesala, Espoo (FI)

(73) Assignee: Teknologian tutkimuskeskus VTT, Espoo (FI)

(*) Notice: Subject to any disclaimer, the term of this patent is extended or adjusted under 35 U.S.C. 154(b) by 468 days.

(21) Appl. No.: 12/160,801

(22) PCT Filed: Jan. 12, 2007

(86) PCT No.: PCT/FI2007/000013
§ 371 (c)(1),
(2), (4) Date: Mar. 29, 2010

(87) PCT Pub. No.: WO2007/080221

PCT Pub. Date: Jul. 19, 2007

(65) Prior Publication Data
US 2010/0186523 A1    Jul. 29, 2010

(30) Foreign Application Priority Data

Jan. 13, 2006 (FI) ............................ 20060027

(51) Int. Cl.
*G01N 1/22* (2006.01)
(52) U.S. Cl. ............... 73/863.51; 73/863.53; 73/863.58; 73/863.81
(58) Field of Classification Search ............ 73/863.51, 73/863.53, 863.58, 863.71, 863.91
See application file for complete search history.

(56) References Cited

U.S. PATENT DOCUMENTS

| | | | | |
|---|---|---|---|---|
| 2,447,595 A | * | 8/1948 | Pigott et al. | 73/863.43 |
| 4,008,620 A | * | 2/1977 | Narato et al. | 73/864.34 |
| 5,058,440 A | * | 10/1991 | Graze, Jr. | 73/863.83 |
| 5,161,417 A | * | 11/1992 | Strong et al. | 73/863.86 |
| 5,184,501 A | * | 2/1993 | Lewis et al. | 73/23.31 |

(Continued)

FOREIGN PATENT DOCUMENTS

EP 0550045 7/1993

(Continued)

OTHER PUBLICATIONS

Béla Leffler, "Stainless—Stainless Steels and Their Properties", Aug. 16, 2001.*

(Continued)

*Primary Examiner* — David Rogers
(74) *Attorney, Agent, or Firm* — Fay Sharpe LLP (57) ABSTRACT

In the method, for collecting and diluting a gaseous sample disposed at a temperature substantially higher than the normal temperature from a sample space (2), a flow of sample is collected into a sampling tube (3); the flow of sample is introduced from the sampling tube into a sample channel (8) formed by a gas permeable first jacket (7); dilution gas is introduced into a dilution gas space (10) formed by a second jacket (9) enclosing the first jacket and connected by its end to the sampling tube, and further from it, through the first jacket into the sample channel; and heat is conducted from the sample space (2) into the dilution gas space (10) for warming up the dilution gas that comes into contact with the sampling tube (3). According to the invention, in the method, a substantially laminar protection flow, which encloses the flow of sample being released from the sampling tube (3) into the sample channel (8) and is disposed longitudinally to the sample channel, is formed from the warmed up dilution gas.

9 Claims, 4 Drawing Sheets

U.S. PATENT DOCUMENTS

| | | | |
|---|---|---|---|
| 5,231,865 A * | 8/1993 | McDermott et al. | 73/28.04 |
| 5,337,595 A * | 8/1994 | Lewis | 73/23.31 |
| 5,438,885 A * | 8/1995 | Zelazny | 73/864.71 |
| 6,021,678 A | 2/2000 | Vardiman | |
| 6,178,830 B1 * | 1/2001 | Freud | 73/863.51 |
| 6,823,748 B2 * | 11/2004 | Silvis et al. | 73/863.03 |
| 6,857,327 B2 * | 2/2005 | Silvis et al. | 73/863.11 |
| 7,044,009 B2 * | 5/2006 | Graze, Jr. | 73/863.03 |
| 7,610,793 B2 * | 11/2009 | Liu et al. | 73/28.01 |
| 2003/0232449 A1 | 12/2003 | Mikkanen | |
| 2008/0087107 A1 * | 4/2008 | Silvis et al. | 73/863.02 |

FOREIGN PATENT DOCUMENTS

| | | |
|---|---|---|
| EP | 550045 A1 * | 7/1993 |
| EP | 1243908 | 9/2002 |
| JP | 57016333 | 1/1982 |
| JP | 2000/329661 | 11/2000 |
| JP | 2004205253 | 7/2004 |

OTHER PUBLICATIONS

Written Opinion for International Patent Application PCT/FI2007/000013, Jan. 13, 2006.*

* cited by examiner

DILUTING SAMPLER AND A METHOD FOR COLLECTING AND DILUTING A GASEOUS SAMPLE

FIELD OF THE INVENTION

The present invention relates to the follow-up and monitoring of emissions produced by various combustion processes, such as by the reactors of power plants or the engines of vehicles. The invention relates to a diluting sampler for collecting a gaseous sample disposed at a temperature substantially higher than a normal temperature from a sample space. The invention also relates to a method for collecting a sample of the aforementioned kind from a sample space and for diluting it.

BACKGROUND OF THE INVENTION

The number and quality of gases and particles being released from combustion processes are analyzed in different ways, both because of environmental decrees and for the purposes of process regulation. From an analysis standpoint, some challenging characteristics are associated with combustion processes, one of the most significant ones being the temperature. For example, the internal temperature of a chimney of a power plant near the reactor can be even much more than a thousand degrees Celsius. Moreover, even rather strongly corrosive agents and a plurality of various particles can flow in the chimney. Introducing a complicated, susceptible electronic measuring device into conditions such as these is impossible in practice due to durability of the materials alone, not to speak of the particle and other materials being accumulated on all surfaces and clogging the device very fast. So usually, the analysis of particles and gases is based on sampling and transporting the sample typically in a cooled and diluted form to be analyzed outside the process being measured.

In sampling it is very important that the sample is cooled and "extinguished" as fast as possible after taking from the process. As a result of various chemical and physical phenomena, the molecules and particles of a sample to be led freely out of the process e.g. along a simple steel pipe tend to change as the temperature drops and the gas is allowed to come into free contact with the gradually cooling walls of the pipe. Herein, the term "extinguishing" generally refers to stopping the chemical and physical processes such as these. The extinguishing is achieved by mixing the sample e.g. with cooled nitrogen or with some other inert gas. At the same time, the sample is diluted to suit the analysis.

For sampling, in which the sample is introduced from a sample space into a sampler and diluted as near as possible to the sample space prior to introducing it further into an analysis device, several solutions are known. As the outermost part, a typical sampler is provided with a tip part projecting into the sample space, through which the flow of sample is introduced into the sampler. The tip part may be a simple one, possibly a metal tube bent to be curved. After the tip part, a sampler is usually provided with a dilution part having a sample channel formed by a porous wall, the sample channel being enclosed by a dilution gas space formed by an impermeable wall. Dilution gas is introduced into the dilution gas space while maintaining in the dilution gas space a pressure higher than that in the sample channel. The pressure difference makes the dilution gas flow through the porous wall into the sample space, thereby diluting and cooling the sample. The circumference of the dilution gas space may also be provided with a cooling agent space for adjusting the temperature of the dilution gas as desired.

These structures have one very significant drawback. A dilution gas which is cooler than the sample and, especially, the walls of the sample channel and dilution space, attached by their ends to the tip part, cool the metal tube of the tip part in the vicinity of the orifice situated on the side of the dilution part thereof. An inner surface of a metal tube that is cooler than the sample acts as an efficient substrate for condensation of gases and accumulation of particles. A material remaining on such a cooler surface means losses of the constituents to be examined in the sample, which results in an erroneous analysis result. On the other hand, a material that has been accumulated on a cool surface can, at some later point, at a higher temperature, come again unstuck, thereby causing distorted results when analyzing the sample. The phenomenon described is the stronger the higher is the temperature difference between the sample space and the dilution gas. The liquid filled cooling agent space possibly included in the sampler and enclosing the dilution gas space enhances the cooling described even more. In typical solutions, the situation is partly also impaired by the dilution gas that hits the flow of sample perpendicularly from the side, the swirling of the sample flow caused by which dilution gas adds to the possibilities of the hot sample gas of getting into contact, at the beginning of the dilution part, with the wall of the sample channel that is cooler than the sample. In that case, there is a risk of material condensing from the sample, besides the tip part, also in the wall of the sample channel.

One prior-art solution of the kind described above is presented in patent publication U.S. Pat. No. 6,021,678 A. The basic problems are the same as in other known solutions. In this solution, too, the dilution gas is e.g. introduced, perpendicularly from the side, into a sample channel serving as an extension to the tip part and having an inner diameter of the same size with it. Thus, there is inevitably swirling at the beginning of the sample channel. As it is impossible in that case to efficiently prevent the sample from getting into contact with the wall of the cool sample channel, the publication describes how in the arrangement, preferably, the dilution gas to be introduced into the dilution gas space is kept at a higher temperature than the condensation temperature. Contrary to what one normally aims to do, one does not try to cool the sample quickly after taking from the sample space, but it is kept at a high temperature. This leads easily to the problems with the changes in the sample as described above. However, in several solutions, cooling is necessary prior to the analysis, so the solution just postpones the problems associated with the cooling without solving them. The heating of the dilution gas also makes the equipment more complicated.

Known from patent publication US 2005/0236040 is a solution in which a sample channel extending into a diluter is enclosed by a concentric jacket-like protection gas channel, into which hot inert gas is introduced. Thus, the sample is introduced into the diluter so that is enclosed by hot protection gas. In order that the sample flow and the wall of the sample channel would be maintained at the temperature of the sample space all way to the diluter, the protection gas channel must begin already on the side of the sample space. Providing a device with this kind of protection gas channel with all the necessary valves and heaters is a very complicated and expensive solution. In addition, the higher is the temperature of the sample space, the more difficult it is in practice to keep the high temperature of the sample and the protection gas all the way from the sample space to the diluter.

OBJECTIVE OF THE INVENTION

The objective of the invention is to alleviate the disadvantages referred to above. One specific objective of the invention is to achieve a novel diluting sampler that is simple in structure and efficiently prevents the losses of sample material. It is also an objective of the invention to disclose a novel method for collecting and diluting a gaseous sample, which method also efficiently prevents the losses of sample material.

SUMMARY OF THE INVENTION

The diluting sampler of the invention for collecting a gaseous sample disposed at a temperature higher than the normal temperature from a sample space comprises, first of all, a sampling tube having a first end for guiding the flow of sample into the sampling tube, as well as a second end. A normal temperature means the reference temperature of 20° C. (293K) known e.g. in the gas industry. A gaseous sample refers generally to samples consisting of gases, which may, however, contain both particles and liquid drops. The sample space may be e.g. the chimney of a reactor of a power plant or the exhaust gas duct of a combustion engine. In addition, the sampler includes a diluter for receiving a flow of sample from the aforementioned second end of the sampling tube and for diluting the sample to a desired concentration.

The diluter includes a tubular, gas permeable first jacket forming a sample channel into which the second end of the sampling tube opens. The diluter also includes a tubular second jacket impermeable to gas that encloses the first jacket and forms between the first jacket and the second jacket a dilution gas space for the dilution gas to be introduced through the first jacket into the sample channel. The second jacket is attached by its end situated on the side of the sampling tube to the sampling tube at a first connecting point. The gas permeable jacket can consist e.g. of metal that that has been prepared by sintering or otherwise arranged to be porous. By introducing into the dilution gas space the desired dilution gas, e.g. nitrogen, while at the same time keeping in the dilution gas space a pressure that is higher than that of the sample channel, the dilution gas is made flow through the porous wall into the sample channel and mix with the sample. Besides a diluting effect, an inert dilution gas substantially cooler than the sample results in cooling and extinguishing of the sample, that is, stopping of the chemical and physical processes that change the composition of the sample.

Similarly to the known devices, the sampler can preferably be so installed that the diluter extends, at its end situated on the side of the sampling tube, into the sample space. In this manner, heat is allowed to be conducted from the sample space into the dilution gas space, which results in heating of the dilution gas. In this manner, by heating an originally cool dilution gas in the vicinity of that end of the dilution gas space which is situated on the side of the sampling tube, the cooling of the second end of the sampling tube that is situated on the side of he diluter is reduced to some extent, and thus the losses of the sample material are reduced as well. By utilizing the heat energy contained in the sample space for the heating, the sampler necessitates no complicated heating means that would incur additional expenses.

According to the invention, the outer diameter of the second end of the sampling tube is smaller than the inner diameter of the first jacket; and the aforementioned second end of the sampling tube extends into the first jacket to a second distance from the first connecting point for guiding the dilution gas so as to form a substantially laminar protection flow disposed longitudinally to the sample channel and enclosing the flow of sample. Herein and hereinafter, a distance is used to mean the distance in the longitudinal direction of the sample channel. As the outer diameter of the sampling tube is smaller than the inner diameter of the sample channel, a free space is left between that portion of the sampling tube which extends into the sample channel and the first jacket that forms the sample channel. Due to the effect of the wall of the sampling tube, the dilution gas that enters this free space through the gas permeable first jacket and that has been warmed up with the heat energy conducted from the sample space is directed so as to enclose the sample flow being released from the sampling tube into the sample channel, so that it forms a substantially laminar flow disposed in parallel to the flow of sample. In this manner, in the diluter of the invention, the flow of sample is introduced into the sample channel within a protection flow warmer than the original temperature of the dilution gas and it does not come into contact with the wall of the sample channel at the beginning of the diluter. At first, the flow of sample is mixed with the warmed up dilution gas prior to facing the cool dilution gas. Using a laminar protection flow efficiently avoids the swirling of the sample flow right at the beginning of the sample channel, which could cause the sample getting into contact with the cool surface of the first jacket. Moreover, the structure can be implemented so that the cool first jacket is not in direct contact with the sampling tube but is attached to it via the second jacket warmed up by the sample space. This for its part efficiently reduces the cooling of the wall of the sampling tube.

In one preferred embodiment of the invention, the diluter also includes a gas tight third jacket enclosing the second jacket and forming between the second jacket and the third jacket a cooling agent space for cooling the dilution gas with a cooling agent to be introduced into the cooling agent space, which cooling agent can be liquid or gas. By its end situated on the side of the sampling tube, the third jacket is attached to the second jacket at a second connecting point. The heat transfer connection between the sample space and the dilution gas space to be installed so as to extend into the sample space is arranged in this embodiment so that the second connecting point between the third jacket forming the cooling agent space and the second jacket enclosing the dilution gas space is disposed at a first distance, which first distance preferably has at least the size of the aforementioned second distance, from the first connecting point between the second jacket and the sampling tube. When in prior-art samplers, the cooling agent space typically extends through the entire length of the dilution gas space, in this embodiment, the second jacket and the dilution gas space formed by it extrude from within the third jacket through a distance corresponding to the aforementioned first distance. The free portion of this second jacket, not enclosed by the third jacket and the cooling agent space, is in direct contact with the sample space. In that case, heat is allowed to be efficiently conducted from the sample space into the second jacket and further into the dilution gas in the dilution gas space. The heat transfer can be still enhanced e.g. by means of heat transfer ribs attached to the second jacket and adding to the metal surface disposed in conjunction with the sample space. It is also possible to use e.g. metal bars or similar heat transfer elements that extend from the sample space through the second jacket into the dilution gas space and conduct heat well. When the first distance has at least the size of the second distance, the heat transfer connection extends into the dilution part at least as far as the sampling tube. This is to ensure that the dilution gas is heated through a sufficiently long distance to prevent cooling of the portion extending into the sample channel of the entire sampling tube.

In one preferred embodiment of the invention, in the vicinity of the second end, the sampling tube is provided with a throttling to accelerate the flow speed of the sample. A throttling is used to mean a narrowing in the inner diameter of the sampling tube. Accelerating the sample flow makes sure that the sample is introduced at a sufficient rate directly into the inside of the sample channel as a laminar flow enclosed by the aforementioned protection flow without the sample remaining swirling at the mouth of the sampling tube.

In one embodiment of the invention, the prevention of formation of cold surfaces which act as substrates for the accumulation of sample material is enhanced by the fact that the sampling tube includes a heat insulator, adapted in the vicinity of the second end to extend to a distance from the first connecting point on its both sides. The fact that the heat insulator extends over the aforementioned first connecting point on its both sides is important because usually the metallic second jacket that conducts heat well acts as an efficient heat sink cooling the sampling tube.

In addition, the sampler can naturally also include e.g. a pump for suctioning the flow of sample into the sampler, as well as various other channels and valves for feeding the dilution gas and the cooling agent into the dilution gas space and the cooling agent space. The sampler can further include fastening means for fastening the sampler to the wall of the sample space. When analyzing a process in the starting phase of a combustion process, when the entire sample space has not been warmed up to its final temperature and the heating of the dilution gas is not at its most efficient point, there may also be heating means in the vicinity of the sampling tube and the connecting point of the diluter for heating up the dilution gas and/or the sampling tube. A heating collar fitted about the circumference of the sampling tube or that of the first jacket may act as this kind of heating means.

The material of the sampling tube that protrudes directly into the sample space containing hot sample gas should consist of some metal mixture that remains unchanged preferably even at temperatures of 1200 to 1400° C. without material being released from it. In this manner, the sampling tube preferably is made e.g. from austenitic stainless steel that withstands high temperatures. One preferred steel of this type contains 0.08% carbon, 21% chrome, 11% nickel, as well as silicon, nitrogen and cerium. In a commercial form, this kind of steel is known with the brand name Sandvik 253 MA. Besides the sampling tube, also the parts of the diluter are preferably made from a corresponding material that suites high temperatures.

It is obvious to a person skilled in the art that the dimensioning of the parts of the sampler depends, in the first place, on the intensity and velocity of the flow desired for the analyzer, as well as on the desired sample dilution ratio. On the other hand, the dimensioning is also affected by the temperature difference between the sample space and the dilution gas. When looking for suitable dimensions, it is possible to use e.g. modeling. In one preferred embodiment of the invention, the outer diameter of the second end of the sampling tube is about 10 mm; the inner diameter of the gas permeable first jacket is about 15 to 20 mm; the aforementioned first distance is about 20 mm; and the second distance between the second end of the sampling tube and the first connecting point is about 10 to 15 mm. In practical tests, a dimensioning such as this has been found to considerably decrease the losses of sample material compared to a prior-art sampler.

In the method of the invention for collecting from a sample space a gaseous sample disposed at a temperature substantially higher than the normal temperature and for diluting the sample, a flow of sample is collected into a sampling tube and introduced from the sampling tube into a sample channel formed by a gas permeable first jacket. In the method, also dilution gas is introduced into a dilution gas space formed by a second jacket enclosing the aforementioned first jacket and attached by its end to the sampling tube, and from it further through the aforementioned gas permeable first jacket into the aforementioned sample channel. Preferably, some inert gas disposed at a temperature substantially higher than the normal temperature is used for the dilution gas, which gas, when mixed with the sample, enables one to rapidly cool the sample and to stop the change processes affecting its composition. The dilution gas can be e.g. nitrogen.

In addition, in the method, heat is conducted from the sample space into the dilution gas space to warm up the dilution gas that comes into contact with the sampling tube. The conduction of heat can be implemented so that through a given stretch, at its end situated on the side of the sampling tube, the second jacket is arranged into a direct contact with the sample space. Heating the dilution gas in the vicinity of the end of the dilution gas space decreases the cooling of the sampling tube and thus the accumulation of sample material on the cool surface. As the heating utilizes the heat energy of the sample space, no external feeding of heat energy is needed, which makes the solution very simple and advantageous.

According to the invention, in the method, from the warmed up dilution gas, a substantially laminar protection flow disposed in parallel to the flow of sample and enclosing the flow of sample being released from the sampling tube into the sample channel is formed. The guiding of the warmed up dilution gas can be implemented e.g. by introducing the end of the sampling tube that is smaller than the sample channel into the sample channel through a given length. Introducing the flow of sample into the sample channel under the protection of a dilution gas flow formed from the warmed up dilution gas considerably decreases both the cooling of the second end of the sampling tube, i.e. of the end that is situated on the same side with the diluter and the swirling of the flow of sample at the beginning of the diluter, which would result in the flow of sample getting into contact with the wall of the sample channel that is cooler than the sample. This minimizes the condensation of the materials and particles of the sample on the walls of the sampling tube and the sample channel.

In one embodiment of the invention, the flow of sample is accelerated in the sampling tube in the vicinity of the end thereof that is situated on the side of the diluter. This ensures fast introduction of the flow of sample into the sample channel inside the diluter, which in turn prevents swirling of the flow of sample at the beginning of the sample channel.

In one embodiment of the invention, the prevention of creation of cool surfaces is, in addition, enhanced so that heat is prevented from being conducted from the sampling tube into the second jacket connected to it. This can be implemented e.g. by means of a heat insulator provided in the sampling tube and extending, at the end thereof that is situated on the side of the diluter, past the aforementioned first connecting point.

The invention achieves considerable improvements compared to prior-art samplers and sampling methods. The invention enables sampling from processes with very high temperatures such as more than 1000° C. with substantially lesser material losses compared to prior-art solutions. The solutions of the invention are also very simple; they do not necessitate any external heat feeding means to warm up the dilution gas.

LIST OF FIGURES

In the following section, the invention will be explained in detail with reference to the accompanying drawings, in which.

DETAILED DESCRIPTION OF THE INVENTION

Figure 1:
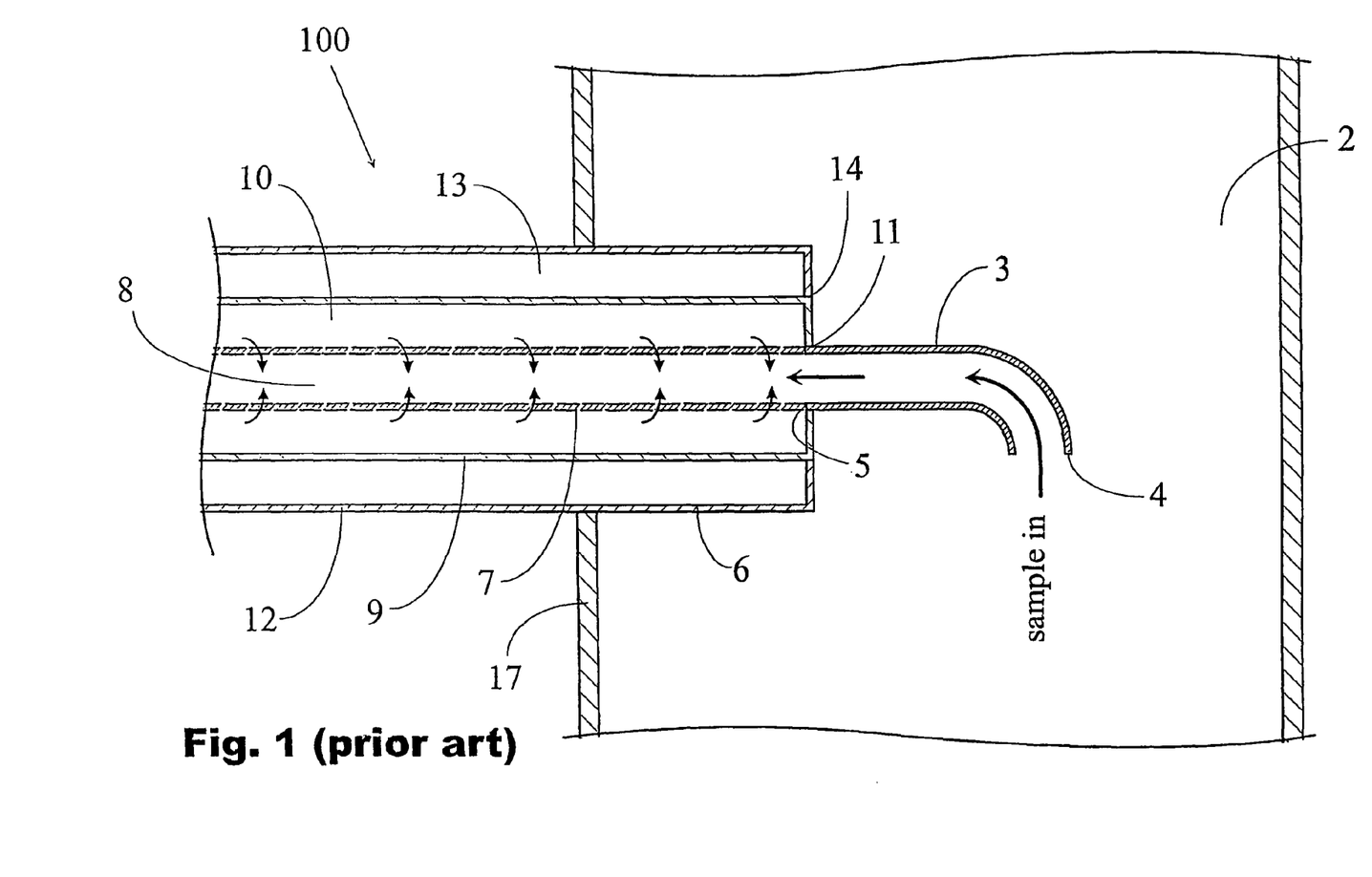
FIG. 1 illustrates the structure of a typical prior-art sampler.
Figure 2:
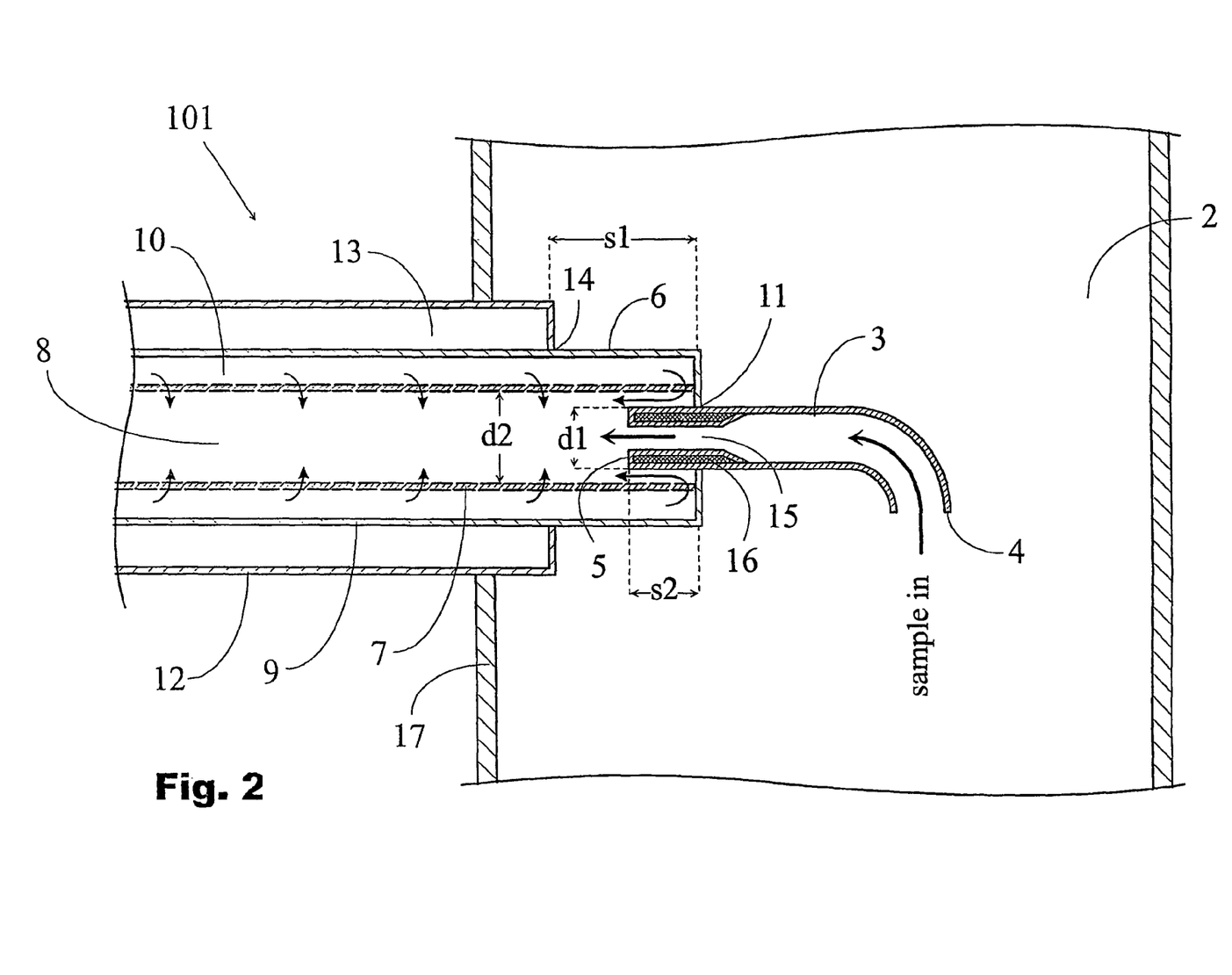
FIG. 2 illustrates the structure of one sampler of the invention.

In order to facilitate the comparison, the corresponding parts of samplers 100, 101 of FIG. 1 (prior-art) and FIG. 2 (the invention) are denoted by the same reference numerals. Samplers 100, 101 presented in the figures in cross sections are installed to extend into a sample space 2, with a gaseous sample flowing therein. The next explanation concerns both samplers 100, 101, where appropriate. Sampler 100, 101 includes a sampling tube 3 having a first end 4 opening into the sample space 2 and a second end 5. In the vicinity of the first end 4, the sampling tube 3 is bent to be in parallel to the gas flow of the sample space to facilitate the introduction of the sample into the sampling tube. Sampler 100, 101 also includes a diluter 6 for receiving a flow of sample from the sampling tube 3 and for diluting the sample. The diluter 6 has a tubular porous first jacket 7, within which there is a sample channel 8, into which the second end of the sampling tube opens. The first jacket is enclosed by a substantially concentric tubular second jacket 9 impermeable to gas, which jacket defines a dilution gas space 10 that encloses the sample channel. The second jacket 9 is in turn enclosed by a substantially concentric, tubular third jacket 12 impermeable to gas, within which there is a cooling agent space 13, encircling the second jacket. The second jacket is impermeably attached to the sampling tube at a first connecting point 11 and the third jacket is attached to the second jacket at a second connecting point 14. In sampler 100 of FIG. 1, at its end, the first jacket 7 is attached to the sampling tube 3 and in sampler 101 of FIG. 2 to the second jacket 9. In FIGS. 1 and 2, the connecting means between samplers 100, 101 and the wall 17 of the sample space, as well as the channels, valves and pumps necessary in the filling of the dilution gas and cooling agent spaces 10, 13 have been omitted as they are known to a person skilled in the art and of secondary importance with respect to the substantial content of the invention. The pump possibly needed for the suction of the flow of sample into the sampler has also been omitted.

The main features of the functioning of samplers 100, 101 are described in short as follows. When a hot sample is being introduced as a continuous flow, for example, by suctioning using a pump into the sampling tube 3 via the first end 4 thereof and further into the sample channel 8, inert dilution gas such as nitrogen, which is substantially cooler than the sample, is being introduced at the same time into the dilution gas space 10. By maintaining in the dilution gas space 10 a pressure higher than that of the sample channel 8, the dilution gas is made flow through the porous first jacket 7 into the sample channel 8 and made get mixed with the flow of sample. In this manner, by rapidly mixing the sample with cool, inert dilution gas, besides adjusting the desired concentration, also the ending of the chemical and physical processes that change the sample is achieved. This ensures that the diluted and cooled sample to be finally introduced into the analyzer corresponds to the conditions of the sample space with respect to its composition. Sampler 100 of FIG. 1 has, however, a very significant disadvantage that impairs the reliability of the results. The sample space may have a temperature of hundreds, even over a thousand, of degrees of Celsius. Naturally, the sampling tube 3 disposed in the sample space tends to warm up to this temperature of the sample space. However, the dilution gas as well as the second jacket attached to the sampling tube at the first connecting point and enclosing the dilution gas, which are both cooler than the sample, cause the fact that the sampling tube tends to cool near the second end 5. The cooling effect is also enhanced by the cooling agent space 13 enclosing the dilution gas space 10 as well as by the third jacket 12 enclosing the cooling agent space and conducting heat well. The inner surface of the sampling tube that is cooler than the sample acts as a substrate for the accumulation and condensation of the particles and gases of the sample. Further, as a result of the swirling caused by the dilution gas that flows into the sample directly from the side, the sample can get into contact with the cool first jacket 7 at the beginning of the sample channel. Material that accumulates on cool surfaces distorts the analysis results of a diluted sample.

In the sampler of the invention shown in FIG. 2, the second connecting point 14 between the third jacket 12 and the second jacket 9 is, in the longitudinal direction of the sample channel 8, disposed at a fist distance s1 from the first connecting point 11 between the second jacket 9 and the sampling tube 3. In this manner, the second jacket 9 enclosing the dilution gas space 10 is in a direct contact with the sample space 2 through a stretch corresponding to the aforementioned first distance. In that case, along the aforementioned length, heat is conducted from the sample space 2 through the second jacket 9 into the dilution gas disposed in the dilution gas space 10. Naturally, the warming-up of the dilution gas and of the second jacket decreases the cooling of the sampling tube 3. In addition, the outer diameter d1 of the sampling tube at the second end 5 of the sampling tube is smaller than the inner diameter d2 of the first jacket 7 that forms the sample channel 8, and the sampling tube extends into the first jacket 7 to a second distance s2 from the first connecting point 11. Due to the effect of the sampling tube 3, the warmed up dilution gas, flowing from the dilution gas space 10 into a space disposed between the second jacket 9 and a portion of the sampling tube 3 that extends into the second jacket, is directed to form a protection flow disposed in parallel to the sample channel 8 and enclosing the flow of sample being released from the sampling tube 3. This protection flow prevents the sample, at the beginning of the sample channel 8, from getting into contact with the inner surface of the first jacket 7 that is cooler than the sample. To ensure this, the second end 5 of the sampling tube 3 is provided with a throttling 15, in which the velocity of the flow of sample increases prior to getting into the sample channel 8. Because irrespective of the heating, the temperatures of the dilution gas, which flows into the sample channel 8 in the vicinity of that end of thereof which is situated on the side of the sampling tube 3, as well those of the second jacket 9 can be somewhat lower than the temperatures of the sample, the second end 5 of the sampling tube shown in the figure is provided with a heat insulator 16 that extends from the second end of the sampling tube past the first connecting point 11 between the sampling tube 3 and the second jacket 9, to prevent the inner surface of the sampling tube from cooling.

The sampling tube 3 of sampler 101 of FIG. 2 and the jackets of the diluter 6 are made from stainless steel Sandvik 253 MA that withstands high temperatures. The outer diameter d1 of the second end 5 of the sampling tube 3 is about 10 mm; the inner diameter d2 of the gas permeable first jacket is about 15 mm; the first distance s1 is about 20 mm; and the second distance s2 between the second end 5 of the sampling tube and the first connecting point 11 is about 10 mm. However, these are not the only functional dimensions but the dimensioning can vary depending e.g. on the intensity of the flow desired for the analyzer and the desired dilution ratio.

Figure 3:
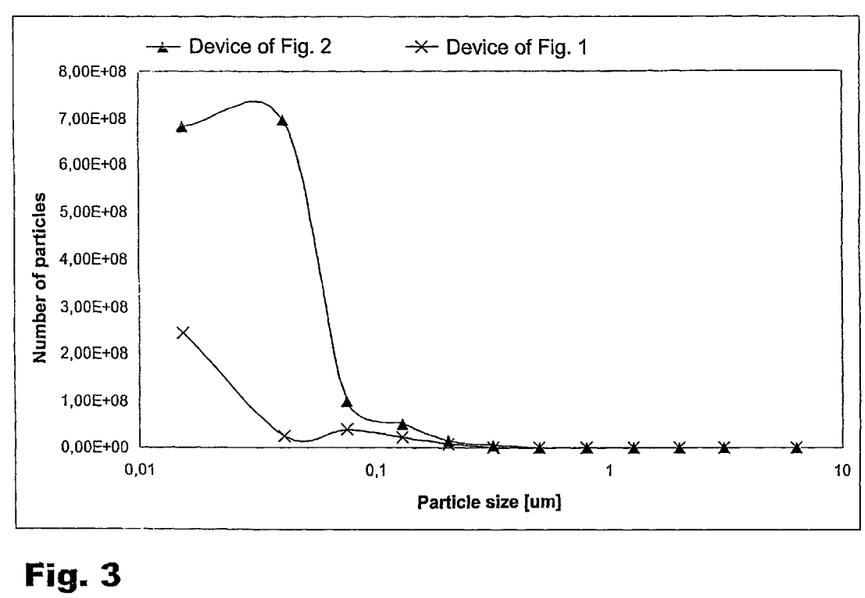
FIG. 3 illustrates the measurement results of the samplers corresponding to FIGS. 1 and 2.

The graphs in FIG. 3 illustrate the advantages to be gained using the sampler in accordance with the invention compared to prior-art devices. The graphs represent measurements made with the same particle analyzer based on the exhaust gases of an engine of a bus. The one measurement used a commercial sampler, resembling in general terms the one shown in FIG. 1 and the other used a sampler in accordance with the invention that was substantially resembling the sampler shown in FIG. 2. The engine was of the DH-10 Euro II type of Volvo. The temperature of the exhaust gases was about 300° C. Air at the temperature of about 25° C. was used as the dilution gas. The horizontal axis of the coordinate system represents the size of the particles and the vertical axis the number of particles detected by the Dekati ELPI measuring device. The number and distribution of the particles were measured at intervals of a second and based on these results mean values of ten seconds visible in the graph were formed. For example, when using a commercial sampler, one detected particles having a diameter of less than 0.04 μm only less than 4% of that amount which was detected when using the sampler of the invention. As one knows that the formation of "cold" surfaces on a sampler is the easier the bigger is the temperature difference between the sample and the dilution gas, the difference in the number of particles with higher temperatures of the sample could be even bigger. As the size of the particles increases, the relative difference gets smaller, which is in harmony with the fact that the accumulation of particles on cold surfaces is known to be the easier the smaller are the particles. The graphs of FIG. 3 are a clear indication of the great improvement to be achieved by the sampler of the invention in the collection and diluting of gaseous samples of high temperatures.

Figure 4:
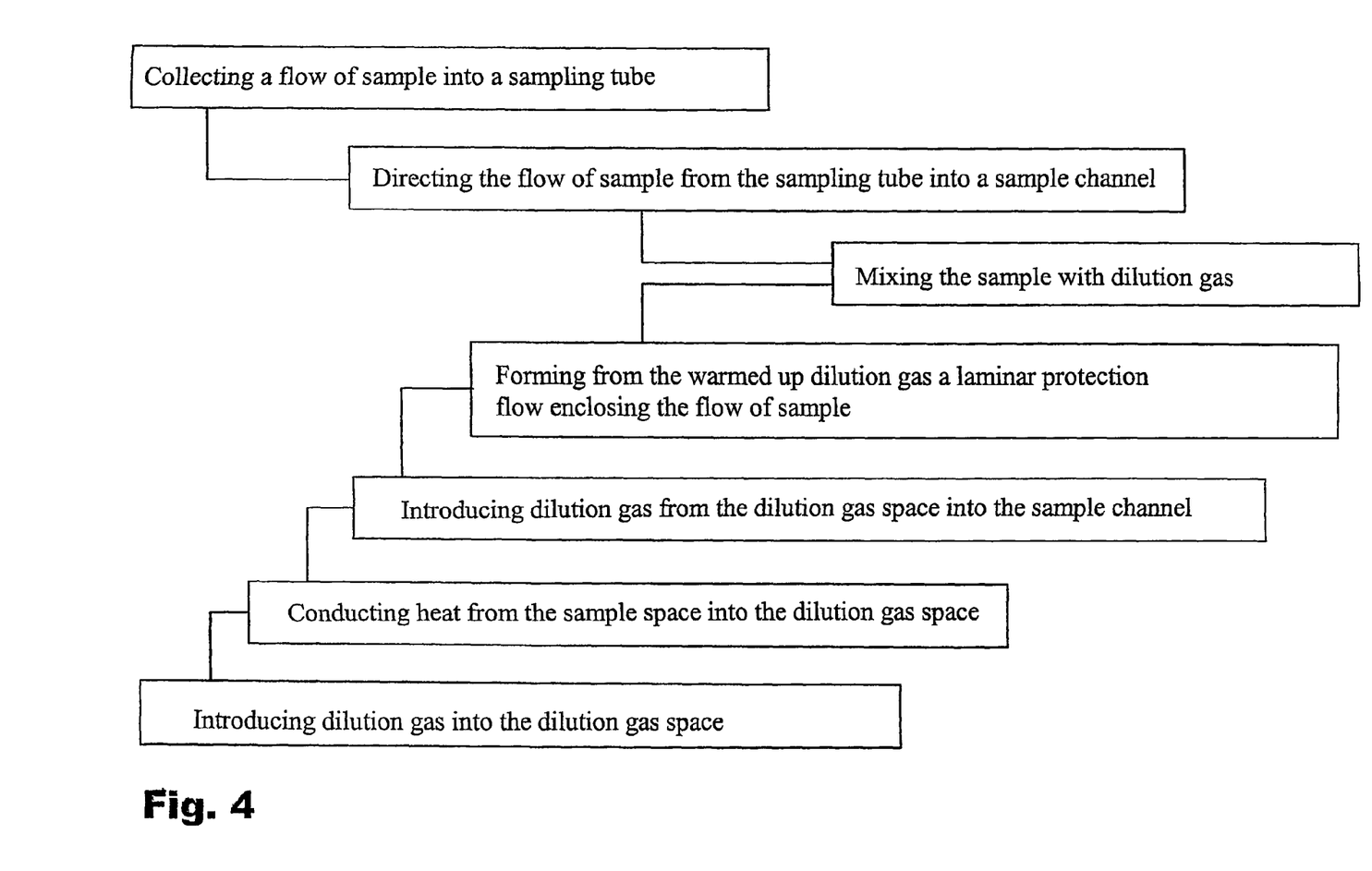
FIG. 4 illustrates the method of the invention.

The method of the invention shown in FIG. 4 does not consist of consecutive phases following each other but it is a constant procedure where all the phases of the figure are continued simultaneously substantially during the whole time the sample is being collected. As for the sample and, on the one hand, also for the dilution gas, the different phases do, however, follow each other, in accordance with the flow diagrammatic representation of FIG. 4. First of all, in the method, a flow of sample is collected into a sampling tube and is directed further into a sample channel formed by a porous jacket. On the other hand, in the method, dilution gas is introduced into a dilution gas space enclosing the sample channel. Also, heat is conducted from the sample space into the dilution gas space, to warm up the dilution gas in the vicinity of the second end situated on the side of the sampling tube. From the dilution gas space, the dilution gas is introduced further through the aforementioned porous jacket into the sample channel. From the warmed up dilution gas, a laminar protection flow enclosing the flow of sample being released from the sampling tube into the sample channel is formed. Finally, the sample that has been introduced into the sample channel within the protection flow is mixed with the cool dilution gas in the sample channel. The method enables one to efficiently dilute and cool a sample without the sample being accumulated on the surfaces of the sampling equipment to any significant extent, which would distort the analysis result.

It must be noted that the invention is not limited merely to the embodiment examples referred to above, but it is obvious to a person skilled in the art that many modifications are possible within the scope of the inventive idea defined by the claims.

The invention claimed is:

1. A diluting sampler for collecting a gaseous sample disposed at a temperature substantially higher than the normal temperature from a sample space, the sampler comprising:
   a sampling tube having a first end for introducing a flow of sample into the sampling tube as well as a second end; and
   a diluter for receiving the flow of sample from the second end of the sampling tube and for diluting the sample, the diluter comprising a tubular:
   gas permeable first jacket forming a sample channel, into which the second end of the sampling tube opens; and
   gas tight second jacket enclosing the first jacket and forming between the first jacket and the second jacket a dilution gas space for the dilution gas to be introduced through the first jacket into the sample channel, the second jacket being connected by its end situated on the side of the sampling tube to the sampling tube at a first connecting point;
   wherein the outer diameter of the second end of the sampling tube is smaller than the inner diameter of the first jacket;
   wherein the second end of the sampling tube projects into the first jacket to a second distance from the first connecting point for directing the dilution gas to form a substantially laminar protection flow disposed longitudinally to the sample channel and enclosing the flow of sample;
   wherein the diluter comprises a gas tight third jacket enclosing the second jacket and forming between the second jacket and the third jacket a cooling agent space for cooling the dilution gas with a cooling agent to be introduced into the cooling agent space, the third jacket being connected by its end situated on the side of the sampling tube to the second jacket at a second connecting point; and
   wherein the second connecting point is disposed at a first distance from the first connecting point in the longitudinal direction of the sample channel, the first distance preferably having at least the size of the second distance for arranging a heat transfer connection between the sample space and the dilution gas space.

2. The diluting sampler as defined in claim 1, wherein, in the vicinity of the second end, the sampling tube has got a throttling for accelerating the flow velocity of the sample.

3. The sampler as defined in claim 1, wherein the outer diameter of the second end of the sampling tube is about 10 mm; the inner diameter of the first jacket is about 15 to 20 mm; and the first distance is about 20 mm and the second distance is about 10 to 15 mm.

4. The diluting sampler as defined in claim 1, wherein the sampling tube is made from austenitic stainless steel resisting high temperatures.

5. The diluting sampler as defined in claim 4, wherein the austenitic stainless steel contains 0.08% carbon, 21% chrome and 11% nickel, as well as silicon, nitrogen and cerium.

6. A diluting sampler for collecting a gaseous sample disposed at a temperature substantially higher than the normal temperature from a sample space, the sampler comprising:

a sampling tube having a first end for introducing a flow of sample into the sampling tube as well as a second end; and a diluter for receiving the flow of sample from the second end of the sampling tube and for diluting the sample, the diluter comprising a tubular:

gas permeable first jacket forming a sample channel, into which the second end of the sampling tube opens; and gas tight second jacket enclosing the first jacket and forming between the first jacket and the second jacket a dilution gas space for the dilution gas to be introduced through the first jacket into the sample channel, the second jacket being connected by its end situated on the side of the sampling tube to the sampling tube at a first connecting point;

wherein the outer diameter of the second end of the sampling tube is smaller than the inner diameter of the first jacket;

wherein the second end of the sampling tube projects into the first jacket to a second distance from the first connecting point for directing the dilution gas to form a substantially laminar protection flow disposed longitudinally to the sample channel and enclosing the flow of sample; and wherein the sampling tube comprises a heat insulator adapted in the vicinity of the second end to extend to a distance from the first connecting point on its both sides to decrease the cooling of the inner surface of the sampling tube.

7. A method for collecting and diluting a gaseous sample disposed at a temperature substantially higher than the normal temperature from a sample space, the method comprising:

collecting a flow of sample into a sampling tube;

directing the flow of sample from the sampling tube into a sample channel formed by a gas permeable first jacket;

introducing dilution gas into a dilution gas space formed by a second jacket enclosing the first jacket and connected by its end to the sampling tube, and further from it through the first jacket into the sample channel;

conducting heat from the sample space into the dilution gas space for warming up the dilution gas which comes into contact with the sampling tube; and forming from the warmed up dilution gas a substantially laminar protection flow which encloses the flow of sample being released from the sampling tube into the sample channel and is disposed longitudinally to the sample channel.

8. The method as defined in claim 7, wherein the flow of sample is accelerated in the sampling tube in the vicinity of the end thereof situated on the side of the sample channel.

9. The method as defined in claim 7, wherein the conduction of heat from the sampling tube into the second jacket connected to it is reduced.

* * * * *